US009585873B2

(12) United States Patent
Stark et al.

(10) Patent No.: US 9,585,873 B2
(45) Date of Patent: *Mar. 7, 2017

(54) ANGIOTENSIN II RECEPTOR ANTAGONIST FOR THE PREVENTION OR TREATMENT OF SYSTEMIC DISEASES IN CATS

(71) Applicants: Marcus Stark, Ingelheim am Rhein (DE); Ulrike D. Sent, Wiesbaden (DE); Ingo Lang, Ingelheim am Rhein (DE)

(72) Inventors: Marcus Stark, Ingelheim am Rhein (DE); Ulrike D. Sent, Wiesbaden (DE); Ingo Lang, Ingelheim am Rhein (DE)

(73) Assignee: Boehringer Ingelheim Vetmedica GmbH, Ingelheim am Rhein (DE)

(*) Notice: Subject to any disclaimer, the term of this patent is extended or adjusted under 35 U.S.C. 154(b) by 0 days.

This patent is subject to a terminal disclaimer.

(21) Appl. No.: 14/293,472

(22) Filed: Jun. 2, 2014

(65) Prior Publication Data

US 2014/0288138 A1 Sep. 25, 2014

Related U.S. Application Data

(63) Continuation of application No. 11/973,250, filed on Oct. 5, 2007, now Pat. No. 8,772,278.

(30) Foreign Application Priority Data

Oct. 6, 2006 (EP) .................................... 06121905

(51) Int. Cl.
| | |
|---|---|
| A61K 31/4184 | (2006.01) |
| A61K 31/00 | (2006.01) |
| A61K 31/41 | (2006.01) |
| A61K 45/06 | (2006.01) |

(52) U.S. Cl.
CPC .......... *A61K 31/4184* (2013.01); *A61K 31/00* (2013.01); *A61K 31/41* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 4,448,778 | A | 5/1984 | Lynch |
| 4,880,804 | A | 11/1989 | Carini et al. |
| 5,846,962 | A | 12/1998 | Suzuki et al. |
| 6,028,091 | A | 2/2000 | Hill |
| 6,204,281 | B1 | 3/2001 | Webb et al. |
| 6,358,986 | B1 | 3/2002 | Schneider |
| 6,410,742 | B1 | 6/2002 | Schneider |
| 6,589,547 | B1 | 7/2003 | Igari et al. |
| 6,737,432 | B2 | 5/2004 | Donsbach et al. |
| 8,871,795 | B2 | 10/2014 | Mohr et al. |
| 2002/0094997 | A1 | 7/2002 | Schneider et al. |
| 2004/0033258 | A1 | 2/2004 | Koike |
| 2004/0110813 | A1 | 6/2004 | Nakatani et al. |
| 2004/0219208 | A1* | 11/2004 | Kawamura ......... A61K 9/1647 424/468 |
| 2005/0070594 | A1 | 3/2005 | Kauschke et al. |
| 2005/0186274 | A1 | 8/2005 | Kohlrausch |
| 2005/0272649 | A1 | 12/2005 | Hruska et al. |
| 2007/0026026 | A1 | 2/2007 | Delmarre et al. |
| 2007/0155679 | A1 | 7/2007 | Daemmgen et al. |
| 2008/0146543 | A1 | 6/2008 | Stark et al. |
| 2012/0095069 | A1 | 4/2012 | Mohr et al. |

FOREIGN PATENT DOCUMENTS

| | | |
|---|---|---|
| CA | 2352436 A1 | 7/2000 |
| CN | 1765362 A | 5/2006 |
| DE | 1023027 B | 1/1958 |
| DE | 10335027 A1 | 2/2005 |
| EP | 1579862 A1 | 9/2005 |
| EP | 2420232 A2 | 2/2012 |
| JP | H11315034 A | 11/1999 |
| WO | 9631234 A1 | 10/1996 |
| WO | 9749392 A1 | 12/1997 |
| WO | 9944590 A1 | 9/1999 |
| WO | 0043370 A1 | 7/2000 |
| WO | 0178699 A2 | 10/2001 |
| WO | 03037876 A1 | 5/2003 |
| WO | 2004014308 A2 | 2/2004 |
| WO | 2004028505 A1 | 4/2004 |
| WO | 2005070463 A2 | 8/2005 |
| WO | 2005123070 A1 | 12/2005 |
| WO | 2006048208 A1 | 5/2006 |
| WO | 2008040774 A2 | 4/2008 |
| WO | 2008110599 A1 | 9/2008 |
| WO | 2010133638 A1 | 11/2010 |

OTHER PUBLICATIONS

The Medical Dictionary (available online at http://medical-dictionary.thefreedictionary.com/kidney+disease; accessed Nov. 1, 2015).*
Guangxi Agricultural College et al., "Oxidation in acidic solutions". Organic Chemistry, Guangxi People's Publishing House, Dec. 1982, p. 235.
Abstract in English of CN1765362, 2006.
Allen, Andrew L., "The Diagnosis of Acetaminophen toxicosis in cats"., The Canadian Veterinary Journal, vol. 44, No. 6, Jun. 2003, pp. 509-510.
Asiedu-Gyekye et al. "Does losartan prevent cerebral edema? A preliminary study using a vascular compartment model". Medical Science Monitor, vol. 9, No. 3, Mar. 2003, pp. BR127-BR130.
Berny et al., "Animal Poisoning in Europe. Part 2: Companion Animals". The Veterinary Journal, vol. 183, 2010, pp. 255-259.
Burnier et al., "Angiotensin II receptor antagonists". The Lancet, vol. 355, 2000, pp. 637-645.

(Continued)

*Primary Examiner* — Craig Ricci
(74) *Attorney, Agent, or Firm* — Michael P. Morris; Wendy M. Gombert

(57) ABSTRACT

A method is described for the treatment of systemic diseases in cats. A composition is administered to a cat, where the composition includes a therapeutically effective amount of angiotensin II receptor 1 (AT-1) antagonist (sartan).

14 Claims, 1 Drawing Sheet

(56) References Cited

OTHER PUBLICATIONS

Champion et al., "Analysis of the Effects of Candesartan on Responses to Angiotensin II in the Hindquarters Vascular Bed of the Cat". Journal of the American Society of Nephrology, vol. 10, 1999, pp. S101-S103.

Cingolani et al., "The Positive Inotropic Effect of Angiotensin II: Role of Endothelin-1 and Reactive Oxygen Species". Hypertension, vol. 47, No. 4, Apr. 2006, pp. 727-734.

Conlon, Peter D., "Nonsteroidal Drugs Used in the Treatment of Inflammation". Clinical Pharmacology, vol. 18, No. 6, 1988, pp. 1115-1131.

Coronel et al., "Hypertension Treatment in Nondiabetic Advanced Chronic Kidney Disease Patients with Irbesartan. Effect on Serum Uric Acid". Abstract, Journal of Hypertension, vol. 23, Supp. 2, 2005, p. S65.

Court et al., "Molecular Basis for Deficient Acetaminophen Glucuronidation in Cats an Interspecies Comparison of Enzyme Kinetics in Liver Microsomes," 1997, Biochemical Pharmacology, vol. 53, pp. 1041-1047.

Ebner et al., "Disposition and Chemical Stability of Telmisartan 1-O-acylglucuronide". 1999, The American Society for Pharmacology & Experimental Therapeutics, vol. 27, No. 10, pp. 1143-1149.

Ettinger et al., "Therapeutic Considerations in Medicine and Disease", Textbook of Veterinary Internal Medicine Diseases of the Dog and Cat, Sixth Edition, vol. 1, Section VI, Table 143, 2005, pp. 530-531.

Garrison et al., "[Pro11, D-Ala12] angiotensin I has rapid onset vasoconstrictor activity in the cat". American Journal of Physiology-Endocrinology and Metabolism, vol. 273, No. 6, 1997, pp. E1059-E1064.

Huskey et al., "N-glucuronidation reactions. I. Tetrazole N-glucuronidation of selected angiotensin II receptor antagonists in hepatic microsomes from rats, dogs, monkeys, and humans." Abstract, Drug Metabolism and Disposition, vol. 21, No. 5, 1993, pp. 792-299 (p. A-9).

Iino et al., "Renoprotective Effect of Losartan in Comparison to Amlodipine in Patients with Chronic Kidney Disease and Hypertension—a Report of the Japanese Losartan Therapy Intended for the Global Reneal Protection in Hypertensive Patients (JLIGHT) Study". Hypertension Research, vol. 27, No. 1, 2004, pp. 21-30.

International Search Report for PCT/EP2007/060531 mailed May 19, 2008.

Israili, Z.H., "Clinical pharmacokinetics of angiotensin II (AT1) receptor blockers in hypertension". Journal of Human Hypertension, vol. 14, Suppl. 1, 2000, pp. S73-S86.

Kemper et al., "Metabolism: A Determinant of Toxicology". Principles and Methods of Toxicology, 5th Edition, Chapter 3, Informa Healthcare USA, New York, NY, 2008, pp. 139-142.

Koide et al., "Hypertrophic response to hemodynamic overload: role of load vs. renin-angiotensin system activation". American Journal of Physiology-Heart, vol. 276, 1999, pp. H350-H358.

Kondo et al., "Characterization of conjugated metabolites of a new angiotensin II receptor antagonist, candesartan cilexetil, in rats by liquid chromatography/electrospray tandem mass spectrometry following chemical derivatization." Abstract, Journal of Mass Spectrometry, vol. 31, No. 8, Aug. 1996, pp. 873-878 (p. A-11).

Kumari et al., "Effect of Pre- and Posttreatment of Losartan in Feline Model of Myocardial Ischemic-Reperfusion Injury". Methods and Findings in Experimental and Clinical Pharmacology, vol. 26, No. 1, 2004, pp. 39-45.

Lazaro et al., "Forum Original Research Communication: Long-Term Blood Pressure Control Prevents Oxidative Renal Injury." Antioxidants & Redox Signaling, vol. 7, Nos. 9 & 10, 2005, pp. 1285-1293.

Lefebvre et al., "Angiotensin-converting enzyme inhibitors in the therapy of renal diseases". Journal of Veterinary Pharmacology and Therapeutics, vol. 27, 2004, pp. 265-281.

Malike et al., "Permethrin Spot on Intoxication of Cats: Literature review and survey of veterinary practioners in Australia". Journal of Feline Medicine and Surgery, vol. 12, 2010, pp. 5-14.

Mathur et al., "Evaluation of a technique of inducing hypertensive renal insufficiency in cats". American Journal of Veterinary Research, vol. 65, No. 7, Jul. 2004, pp. 1006-1013.

Osweiler, Gary D., "Toxicological Concepts: Factors that Influence Toxicology", General Toxicological Principles, in Small Animal Toxicology, Elsevier, Inc., St. Louis, MO, 2006, p. A17.

Perrier et al., "In vitro N-glucuronidation of SB 47436 (BMS 186295), a new AT1 nonpeptide angiotensin II receptor antagonist, by rat, monkey and human hepatic microsomal fractions." Abstract, The Journal of Pharmacology and Experimental Therapeutics, vol. 271, No. 1, Oct. 1994, pp. 91-99 (p. A-10).

Rodriguez-Iturbe et al., "Early treatment with cGMP phosphodiesterase inhibitor ameliorates progression of renal damage". Kidney International, vol. 68, 2005, pp. 2131-2142.

Schiweck et al., "Sugar Alcohols". Ullmann's Encyclopedia of Industrial Chemistry, Wiley-VCH Verlag GmbH & Co. KGaA, Weinheim, 2012, pp. 1-37.

Snively et al., "Chronic Kidney Disease: Prevention and Treatment of Common Complications". American Family Physicians, vol. 70, No. 10, Nov. 2004m pp. 1921-1928.

Stebbins et al., "Spinal angiotensin II influences reflex cardiovascular responses to muscle contraction". American Journal of Physiology, vol. 269, No. 4, Part 2, 1995pp. R864-R868.

Suga et al., "Angiotensin II type 1 receptor blockade ameliorates tubulointerstitial injury induced by chronic potassium deficiency". 2002, Kidney International, vol. 61, pp. 951-958.

Tran et al., "Modulation of microenvironmental pH and crystallinity of ionizable telmisartan using alkalizers in solid dispersions for controlled release". Journal of Controlled Release, vol. 129, No. 1, 2008, pp. 59-65.

Villar et al., "Ibuprofen, Aspirin and Acetaminophen Toxicosis and Treatment in Dogs and Cats". Veterinary Human Toxicology, vol. 40, No. 3, 1998, pp. 156-162.

Web site: www.merck.com "Chronic Kidney Disease," accessed on Dec. 13, 2010.

Web site: www.merck.com "Tubulointerstitial Nephritis," accessed on Jun. 1, 2009.

White, et al., "Effects of the angiotensin II receptor blockers telmisartan versus valsartan on the circadian variation of blood pressure: impact on the early morning period," Amer Journal of Hypertension, vol. 17, Issue 4, 2004, pp. 347-353.

Written Opinion of the International Search Authority for PCT/EP2007/060531 mailed May 19, 2008.

Xiao et al., "Regional Hemodynamic Effects of the AT1 Receptor Antagonist CV-11974 in Conscious Renal Hypertensive Rats". Hypertension, vol. 26, 1995, pp. 989-997.

Grauer, Gregory, "ACE Inhibitors and CKD", 2 pages. [Accessed at : http://www.dvm360storage.com/cvc/proceedings/dc/Urology/Grauer/Grauer,Gregory_ACE_Inhibitors_and_CKD.pdf on Feb. 5, 2015].

Syme et al., "Survival of Cats with Naturally Occurring Chronic Renal Failure Is Related to Severity of Proteinuria". Journal of Veterinary Internal Medicine, vol. 20, No. 3, 2006, pp. 528-535.

Abstract in English of JPH11315034, 1999.

Li et al., "Efficacy evaluation of Telmisartan in treatment of dilated cardiomyopathy with heart failure". Chinese Heart Journal, vol. 18, No. 4, 2006, pp. 427-429.

Lim et al., "Angiotensin II Blockade Reverses Myocardial Fibrosis in a Transgenic Mouse Model of Human Hypertrophic Cardiomyopathy". Circulation, vol. 103, Feb. 2001, pp. 789-791. [Accessed at http://circ.ahaqjournals.org/ on Sep. 3, 2014].

Norikazu et al., "Comparison of angiotensin II receptor antagonists and angiotensin converting enzyme inhibitors on a dog suffering mild mitral insufficiency". Annual Meeting of the Japanese Society of Veterinary Science, vol. 137, 2004, p. 140.

Polzin et al., "Treating Feline Kidney Disease: An Evidence-Baed Approach". North American Veterinary Conference Proceedings, Jan. 7, 2006, pp. 1-6. [Accessed at http://www.iknowledgenow.com/article.cfm?documentID=2817&transactionKey . . . on Dec. 16, 2014].

(56) References Cited

OTHER PUBLICATIONS

Written Opinion of the International Searching Authority for PCT/EP2010/056895 mailed on Aug. 3, 2010.
Hiwada, Kunio, "Presentation of New Drug: Telmisartan". Vascular Biology & Medicine, vol. 3, No. 5, 2002, pp. 571-576.
Ono et al., "Characteristics of the Long-Acting Sartan Telmisartan". Circulation Control, vol. 23, No. 4, 2002, pp. 462-466.
Wienen et al., "A Review on Telmisartan: A Novel, Long-Acting Angiotensin II-Receptor Antagonist". Cardiovascular Drug Reviews, vol. 18, No. 2, 2000, pp. 127-154.
Xue, Jintong. "Chapter 13. Hypertensive Disease". Practical Handbook for the Diagnosis and Treatment of Cardiovascular Disease, First Edition, Zhengzhou University Press, 2005, pp. 480-508.
Honjo et al., "Possible Beneficial Effect of Telmisartan on Glycemic Control in Diabetic Subjects". Diabetes Care, vol. 28, No. 2, Fe. 2005, p498.
Pershadsingh et al., "Insulin-Sensitizing Effects of Telmisartan". Diabetes Care, vol. 27, No. 4, Apr. 2004, p. 1015.
Yoshida et al., "Metabolic effect of AII receptor antagonists." Ketsuatsu (Blood Pressure), vol. 9, No. 8, 2002, pp. 802-806. (Abstract in English).
Buoncompagni et al., "Treatment of Systemic Hypertension Associated With Kidney Disease." Compendium: Continuing Education for Veterinarians, Vetlearn.com, 2013, pp. E1-E6.
Jensen et al., "Plasma renin activity and angiotensin I and aldosterone concentrations in cats with hypertension associated with chronic renal disease." American Journal of Veterinary Research, vol. 58, No. 5, May 1997, pp. 535-540.

* cited by examiner

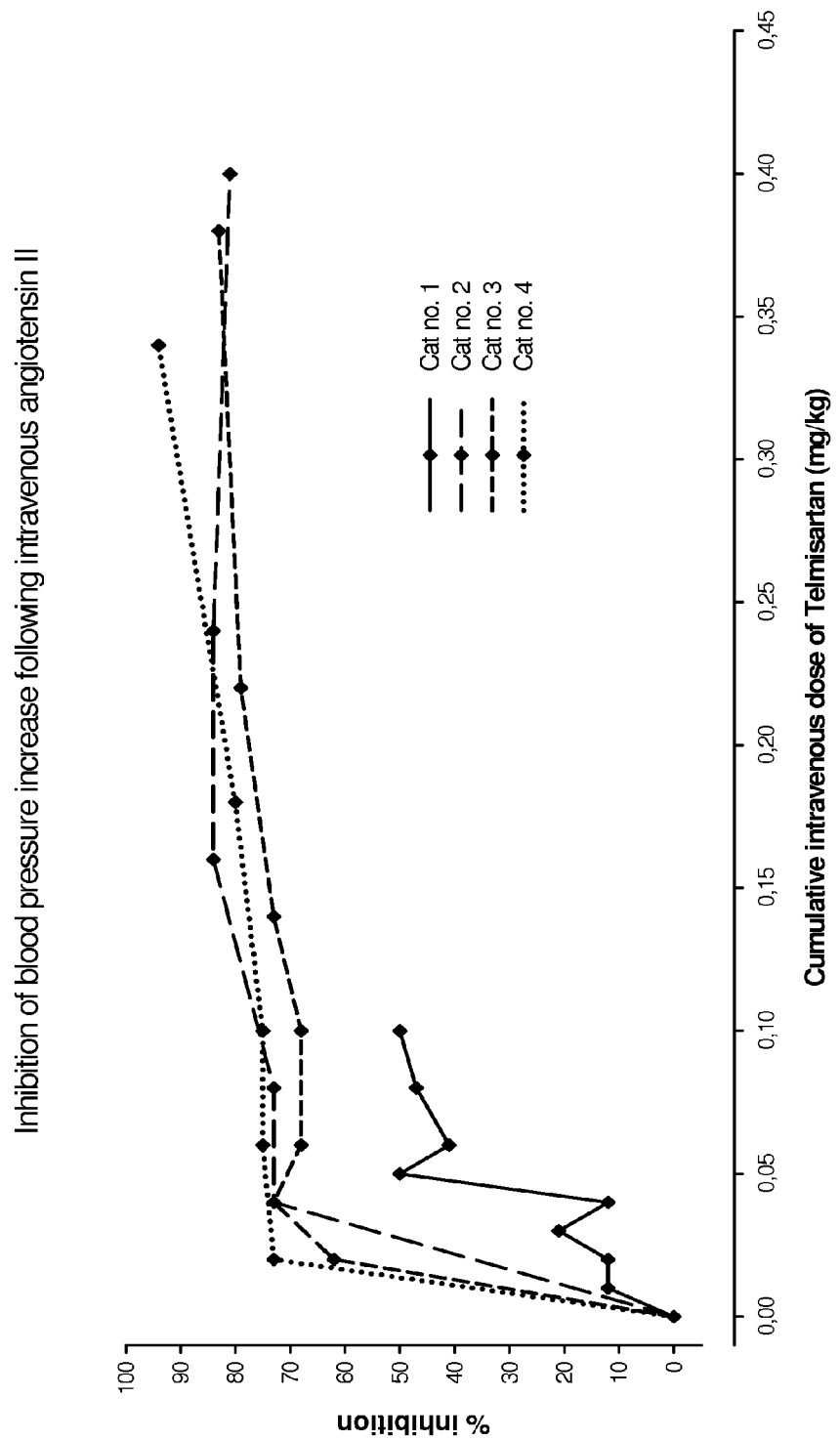

ANGIOTENSIN II RECEPTOR ANTAGONIST FOR THE PREVENTION OR TREATMENT OF SYSTEMIC DISEASES IN CATS

CROSS REFERENCE TO RELATED APPLICATIONS

The present application claims priority to European Application No. EP 06121905, filed Oct. 6, 2006, the disclosure of which is incorporated herein by reference in its entirety.

FIELD OF THE INVENTION

The present invention relates to the field of veterinary medicine, especially to the prophylaxis or treatment of systemic diseases in cats. In particular, the present invention relates to a method of prophylaxis or treatment of systemic diseases in cats, wherein the method comprising administration of a therapeutically effective amount of angiotensin II receptor 1 (AT-1) antagonist (sartan) to a cat in need of such a treatment.

BACKGROUND OF THE INVENTION

The prevalence of renal disease is high in aged cats, whereas chronic renal failure is considered the most important one. The prevalence of chronic kidney disease (CKD) in cats is reported to reach up to 20% with 53% of cats were older than 7 years (Lefebre, Toutain 2004, *J. Vet. Pharm. Therap.* 27, 265-281; Wolf A M *North. Am. Vet. Congress* 2006). Survival in cats with mild to moderate azotemia and extrarenal clinical signs (IRIS stage 2 & 3) ranged from 1 to 3 years. Early management and therapy is considered to successfully influence prognosis for CKD (Wolf A M *North Am. Vet Congress* 2006).

Chronic renal failure (CRF), at least in its final stage is, regardless of the underlying causes, characterized by irreversible structural lesions of the kidney. Thereby, progressive irreversible lesions initially localized to one portion of the nephron (e.g. glomeruli, peritubular capillaries, tubules or interstitial tissue), are eventually responsible for the development of lesions in the remaining, but initially unaffected portions of nephrons due to their functional interdependencies. New nephrons cannot be formed to replace others irreversibly destroyed by disease. In a study of biopsy findings in cats with primary renal azotemia, tubulointerstitial nephritis was observed in 70%, glomerulonephropathy occurred in 15%, lymphoma in 11% and amyloidosis was observed in 2% of the samples. CRF is recognized by reduced kidney function or the presence of kidney damage (Polzin, Osborne, Ross 2005 in: Ettinger S J, Feldman C E (eds.) *Textbook of Veterinary Internal Medicine*, 6$^{th}$, Vol 2. Chapter 260, 1756-1785).

Angiotensin II plays an important part in pathophysiology, particularly as the most potent agent for increasing blood pressure in humans. It is known that in addition to its effect of raising blood pressure Angiotensin II also has growth-promoting effects which contribute to left ventricular hypertrophy, vascular thickening, atherosclerosis, renal failure and stroke. In small animals, inhibition of the effects of Angiotensin II, via either ACE inhibitors have been shown to exhibit renoprotectiv effects through their simultaneous capacity to decrease blood pressure and control proteinuria.

Current therapy aims to delay the progression of the disease in cats by improving renal function, especially glomerular function by maintaining glomerular perfusion. This includes dietary protein restriction, modification of dietary lipid intake, phosphate restriction and treatment with angiotensin-converting enzyme (ACE) inhibitors (P. J. Barber (2004) *The Kidney*, in: Chandler E A, Gaskell C J, Gaskell R M (eds.) *Feline Medicine and Therapeutics*, 3rd edition, Blackwell Publishing, Oxford, UK).

ACE inhibitors, especially enalapril, benazepril, imidapril and ramipril, have been initially developed in small animal medicine to control chronic heart failure (CHF). Based on the pathophysiological role of the renin-angiotensin-aldosterone system (RAAS) in progression of chronic heart failure and in progression of renal damage, these agents have been shown to be useful in the treatment of chronic kidney disease (CKD) in order to delay progression of disease and reduce morbidity and suffering in small animals, including cats. Sound evidence for this is probably the recent approval of benazepril in Europe for the treatment of feline CRF (Lefebre Toutain, 2004 J Vet Pharm Therap 27, 265-281). However, the renoprotection of ACE inhibitor was likely mediated by the effect on proteinuria rather than by blood pressure reduction. This has been shown for ramipril, since the effect on blood pressure was comparable to that of placebo while the proteinuria was reduced (Remuzzi et al., 2006, *J Clin Invest* 116, (2) 288-296).

From a clinical point of view, ACE inhibitors are not the preferred target to block the RAAS because of the lack of specificity for Angiotensin I and the "angiotensin escape" phenomenon where alternate enzymatic pathways such a cathepsin, trypsin or the heart chymase can also convert Angiotensin I. Moreover, during long term treatment with ACE inhibitors, ACE activity is upregulated and Angiotensin I levels are high due the stimulated renin secretion (Burnier & Brunner, 2000, *The Lancet*, 355, 637-645).

Thus, one objective of the present invention consists in providing a new therapeutic approach for the treatment or prophylaxis of cats against chronic kidney disease.

A further more general aspect of the present invention consists in providing a new therapeutic approach for the treatment or prophylaxis of cats against systemic diseases; preferably against systemic diseases which are related to Angiotensin II or associated with the renin-angiotensin-aldosterone system (RAAS).

BRIEF DESCRIPTION OF THE DRAWINGS

FIG. 1: Inhibition of blood pressure increase by angiotensin II receptor 1 antagonist.

DETAILED DESCRIPTION OF THE INVENTION

Before the embodiments of the present invention it shall be noted that as used herein and in the appended claims, the singular forms "a", "an", and "the" include plural reference unless the context clearly dictates otherwise. Thus, for example, reference to "a preparation" includes a plurality of such preparations, reference to the "carrier" is a reference to one or more carriers and equivalents thereof known to those skilled in the art, and so forth. Unless defined otherwise, all technical and scientific terms used herein have the same meanings as commonly understood by one of ordinary skill in the art to which this invention belongs. All given ranges and values may vary by 1 to 5% unless indicated otherwise or known otherwise by the person skilled in the art, therefore, the term "about" was omitted from the description. Although any methods and materials similar or equivalent to those described herein can be used in the practice or testing of the present invention, the preferred methods, devices, and materials are now described. All publications mentioned herein are incorporated herein by reference for the purpose of describing and disclosing the substances, excipients, carriers, and methodologies as reported in the publications which might be used in connection with the invention. Nothing herein is to be construed as an admission that the invention is not entitled to antedate such disclosure by virtue of prior invention.

The solution to the above technical problem is achieved by the description and the embodiments characterized in the claims.

To date, the use of angiotensin II receptor 1 antagonists (sartans) in cats is not described for any indication. Blockage of angiotensin II receptor 1 is a treatment concept which differs from blockage of angiotensin converting enzyme as known from the ACE-inhibitors. Receptor blockage is more specific and complete and further downstream in the physiologic cascade of the RAAS system. The present invention is based on various unexpected findings:

It was surprisingly found that cats tolerate a pharmacodynamically effective dose of sartans. In an open-label study in nondiabetic, hypertensive human patients with proteinuric nephropathies the effects on renal outcome of low (80 mg once daily) and high dose (80 mg twice daily) telmisartan were compared. The results reinforced the concept that more effective RAAS inhibition achieved by a high dose of 160 mg daily. This dose corresponds to a plasma level of about 2800±2400 ng/ml (Cmax±SD), which exceeds the no-effect doses in toxicities studies in animals such as dogs and rats. (Investigator brochure 1994, data on file) The resulting dose of about 2 to 3 mg/Kg body weight and day was thus expected to be toxic in cats. Pilot-toxicity studies have surprisingly shown that such a dose (up to 3 mg/kg) is well tolerable in cats.

Moreover, it was found that sartans effectively blocks the angiotensin II receptor 1 also in cats. This finding was all the more unexpected, as the absolute bioavailability in cats is very low and the mean residence time and plasma half life are rather short in cats as compared to human beings. The oral bioavailability was calculated to 33.6% as compared to human beings. The mean $t_{max}$ oral was 0.44 hours and the $C_{max}$ oral was 138.1 ng/ml. The mean $t_{1/2}$ oral was 2.17 hours. The mean AUC→~oral was calculated to 150 (ng× h/ml), and the mean V/f oral was 20.4 l/kg. The mean AUC→~intravenous was calculated to 385 (ng×h/ml). The mean $t_{1/2}$ intravenous was 2.25 hours and the mean V/f oral was 8.8 l/kg. From this information, which was newly generated, it can be concluded that sartans, preferably telmisartan, can be used to treat cats with systemic diseases, preferably with chronic kidney disease, such as for example chronic renal failure, including chronic renal insufficiency.

TABLE 1

Abbreviations

| Abbreviation | Pharmacokinetic parameters |
|---|---|
| AUC | area under the plasma concentration time curve |
| C max | maximum measured plasma concentration |
| V/f | Volume of distribution (V) whereas f is the absolute bioavailability |
| MRT | mean residence time |
| t ½ | terminal half-live |
| t max | time to reach Cmax |

Thus, according to one embodiment, the present invention relates to a method for the prophylaxis or treatment of a systemic disease in cats, wherein the method comprising administration of a therapeutically effective amount of angiotensin II receptor 1 (AT-1) antagonist (sartan) to that cat in need of such a treatment.

The term "systematic disease" as used herein means but is not limited to cardiovascular such as dilated cardiomyopathy (DCM), mitral valve insufficiency (MI), hypertrophic cardiomyopathy (HCM); and other acquired or hereditary heart diseases, e.g. cardiopulmonary diseases, systemic hypertension for example hypertension associated with renal diseases, chronic renal failure and other vascular diseases, or metabolic disorders such as diabetes mellitus. Thus, according to another aspect, the present invention relates to a method for the prophylaxis or treatment of a systemic disease in cats by the administration of therapeutically effective amount of said angiotensin II receptor 1 (AT-1) antagonist (sartan) to that cat, wherein the systemic disease is selected from the group of cardiovascular diseases, such as dilated cardiomyopathy (DCM), mitral valve insufficiency (MI), hypertrophic cardiomyopathy (HCM) and other acquired or hereditary heart diseases, systemic hypertension, for example hypertension associated with renal diseases, chronic renal failure and other vascular diseases, metabolic disorders like diabetes mellitus.

In humans, angiotensin II receptor 1 (AT1 receptor antagonists (sartans) are known to significantly reduces proteinuria in both diabetic and non-diabetic patients, even in those with mild to moderate chronic renal failure (CRF). Moreover, there is published evidence for the efficacious use of AT1 receptor antagonists for treatment of nephropathies in type II diabetes Cupisti A, et al., 2003, *Biomed Pharmacother*; 57 (3-4):169-172; Rysava R, et al., 2005, *Press Monit*; (10(4):207-213; WO92/10182). In cats tubulointerstitial nephritis is reported to be the major causative (>70%) finding for CRF whereas in human beings and dogs glomerulonephropathy is more prominent compared to cats. Glomerular lesions are more often seen in dogs and humans and consequently the clinical finding of moderate to marked proteinuria, resulting from loss of glomerular permselectivity, is more common in dogs and humans. Tubulointerstitial nephritis as seen in cats showed less proteinuria. Proteinuria is recognized as an important predictor of disease progression in humans and dogs with spontaneous kidney disease and reduction of proteinuria is associated with improved outcome in clinical trials to show the renoprotective effects of blocking the RAAS by either ACE or ARBs in human suffering from nephropathy (Karalliede & Viberti, *J Human Hypertension* 2006). Due to the fact that there is less proteinuria in cats because of the tubulointerstitial origin of CRF, the reduction of proteinuria as renoprotective effect in delaying progression of CRF might be expected to be less important in this species. However, in a clinical field trial an independent and significant correlation between proteinuria (determined as UPC) and survival in cats suffering from CRF have been reported. Surprisingly, even in azotemic cats with only minor proteinuria (acc. to IRIS, UPC <0.25) this correlation was evident (Syme, Elliot 2006, *J Vet Intern Med*, 20, 528-535).

Thus, according to a preferred embodiment the systemic disease is chronic kidney disease, preferably chronic renal failure, e.g. as defined as stage II to IV in Table 2.

The diagnosis of reduced kidney function such as chronic renal failure is based on exclusion of pre- and postrenal causes and standard blood markers, e.g. urea and creatinine in plasma or serum. Abnormal concentrations of these parameters are described as azotemia. Standard urine markers of reduced kidney function include urine specific gravity, proteinuria and others (Polzin D J, Osborne C A, Ross S, 2005: *Chronic Kidney Disease*, In: Ettinger S J, Feldman E C (*ed.*)*Textbook of Veterinary Internal Medicine* 6$^{th}$ edition, W.B. Saunders Company, Philadelphia, USA). The international renal interest society (IRIS) has proposed a staging system based on azotemia to define CRF patients (Polzin D J, 2006: *Treating feline kidney disease: an evidence-based approach, Proceedings of The North American Veterinary Conference*). The main category for staging being plasma creatinine [mg/dl], which is completed by two subcategories independent from stage, urine protein:creatinine ratio (UPC) and blood pressure [mmHg]. With the applied system, feline patients are staged along a continuum of progressive kidney disease.

TABLE 2

Stages of feline chronic kidney disease

| stage | Plasma creatinine (mg/dl) | Comments | Subcategory UPC (independent from stage) | Subcategory systolic blood pressure (mmHg, independent from stage) |
| --- | --- | --- | --- | --- |
| I | <1.6 | Non-azotemic: some other renal abnormality is present | <0.2 = Non-proteinuric | <150 = minimal risk of end-organ damage |
| II | 1.6-2.8 | Mildly azotemic: usually mild clinical signs | 0.2-0.4 = Borderline proteinuric | 150-159 = low risk of end-organ damage |
| III | 2.9-5.0 | Moderately azotemic: many extra renal clinical signs | | 160-179 = moderate risk of end-organ damage |
| IV | >5.0 | Severly azotemic: invasive life support methods required | >0.4 = Proteinuric | ≥180 = high risk of end-organ damage |

Thus, according to a further embodiment, the present invention relates to a method for the prophylaxis or treatment of chronic renal failure in cats, wherein the method comprising administration of a therapeutically effective amount of angiotensin II receptor 1 (AT-1) antagonist (sartan) to that cat in need of such a treatment and wherein said chronic renal failure is characterized by any one of the clinical manifestations as listed in table 2, or any combination thereof. For example, the present invention relates to a method for the prophylaxis or treatment of cats having an plasma creatine of ≥1.6 (mg/dl of blood), and/or having a proteinuric of ≥0.2 (subcategory UPC), wherein the method comprises administration of a therapeutically effective amount of angiotensin II receptor 1 (AT-1) antagonist (sartan) to that cat in need of such a treatment.

A comprehensive list of angiotensin II receptor antagonists can be found on pages 2 to 22 of WO 92/10182 and pages 7 to 18 of WO 95/26188, which all are incorporated herein by reference. Angiotensin II receptor antagonists are described inter alia in EP-A-253310, EP-A-323841, EP-A-324377, EP-A-420237, EP-A-443983, EP-A-459136, EP-A-475206, EP-A-502314, EP-A-504888, EP-A-514198, WO 91/14679, WO 93/20816, WO 02/092081, U.S. Pat. No. 4,355,040, U.S. Pat. No. 4,880,804 and U.S. Pat. No. 6,028,091. Forms which are frequently mentioned are sartans, such as candesartan, eprosartan, irbesartan, losartan, olmesartan, tasosartan, telmisartan or valsartan. Those which are particularly preferred according to the present invention are irbesartan, losartan and telmisartan. All of these sartans, or pharmaceutical salts or polymorphs thereof are well known to a person skilled in the art, and its use is within the meaning of the present invention.

Thus the present invention relates to a method for the prophylaxis or treatment of cats suffering from a systemic disease, preferably from chronic kidney disease, e.g. chronic renal failure, wherein the method comprising administration of a therapeutically effective amount of angiotensin II receptor 1 (AT-1) antagonist (sartan) to that cat in need of such a treatment and wherein the angiotensin II receptor 1 (AT-1) antagonist (sartan) is selected from the group consisting of: candesartan, eprosartan, irbesartan, losartan, olmesartan, tasosartan, telmisartan or valsartan, preferably of irbesartan, losartan and telmisartan.

Telmisartan is an angiotensin II receptor antagonist developed for the treatment of hypertension and other medical indications as disclosed in EP-A-502314. Its chemical name is 4'-[2-n-propyl-4-methyl-6-(1-methylbenzimidazol-2-yl)-benzimidazol-1-ylmethyl]-biphenyl-2-carboxylic acid having the following structure:

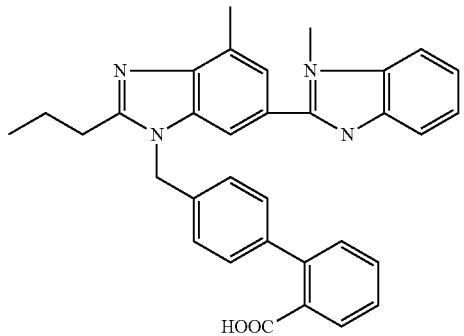

Telmisartan is already sold on the market under the trade name Micardis® (Boehringer Ingelheim, Germany) for treatment/prophylaxis of humans. It exists in two polymorphic forms as disclosed in WO 00/43370, U.S. Pat. No. 6,358,986 and U.S. Pat. No. 6,410,742. Sodium salts of telmisartan and its solvate, hydrate, and hemihydrate are disclosed in WO 03/037876.

Thus, according to a further embodiment, the present invention relates to a method for the prophylaxis or treatment of a systemic disease in cats, preferably of chronic kidney disease, e.g. chronic renal failure, wherein the method comprising administration of a therapeutically effective amount of telmisartan or pharmaceutically acceptable salt thereof, preferably of a telmisartan as mentioned above. More preferably said telmisartan is MICARDIS®.

As already mentioned above, it has been surprisingly found that use of telmisartan effectively inhibits the angiotensin II receptor pressure response in cats. Moreover, it has been surprisingly found that doses of less than 0.05 mg telmisartan per kg body weight of cat led to an inhibition of the blood pressure response of about 75% in the majority of the tested cats. Moreover, a study in laboratory cats was established to investigate the Angiotensin II induced increase in diastolic blood pressure prior to and after administration of telmisartan. This test was established to estimate the potency as well as the duration of action of sartans, in particular of telmisartan in cats. Approximately 24 hours after the last oral dosing, diastolic blood pressure responses to increasing intravenous doses of Angiotensin II were significantly reduced when the target dose of telmisartan was compared with Placebo. Thus it could be concluded that administration of the target dose, despite the short elimination half-life and bioavailability, in the cat given once daily is capable to exhibit the intended pharmacodynamic action and duration.

Thus, according to another aspect, the present invention relates to a method for the prophylaxis or treatment of a systemic disease in cats, preferably of chronic kidney disease, e.g. chronic renal failure, wherein the method comprising administration of a therapeutically effective amount of angiotensin II receptor 1 (AT-1) antagonist (sartan), preferably telmisartan or pharmaceutically acceptable salt thereof, to that cat in need of such a treatment, wherein the therapeutically effective amount of such angiotensin II receptor 1 (AT-1) antagonist is about 0.01 to about 10 mg/kg of body weight. Preferably, said therapeutically effective amount of such angiotensin II receptor 1 (AT-1) antagonist is about 0.05 to about 8 mg/kg of body weight, even more preferably about 0.1 to about 5 mg/kg of body weight, even more preferably about 0.2 to about 4 mg/kg of body weight, even more preferably about 0.3 to about 3 mg/kg of body weight, even more preferably about 0.4 to about 2.5 mg/kg of body weight, even more preferably about 0.5 to about 2 mg/kg of body weight, most preferred about 0.75 to about 1.5 mg/kg of body weight. Thus, said therapeutically effective amount of such angiotensin II receptor 1 (AT-1) antagonist is for example 0.01, 0.02, 0.03, . . . 0.08, 0.09, 0.1, etc.; 0.11, 0.12, 0.13, . . . 0.18, 0.19, 0.2, etc.; 0.21, 0.22, 0.23, . . . 0.28, 0.29, 0.3 etc. . . . ; 0.81, 0.82, 0.83, . . . 0.88, 0.89, 0.9 etc.; 0.91, 0.92, 0.93, . . . 0.98, 0.99, 1.0 etc.; 1.01, 1.02, 1.03, . . . 1.08, 1.09, 1.1 etc.; . . . 1.2, 1.3, . . . 1.8, 1.9, 2.0 etc.; 2.1, 2.2, 2.3, . . . 2.8, 2.9, 3.0 etc.; . . . ; 8.1, 8.2, 8.3, . . . 8.8, 8.9, 9.0 etc.; 9.1, 9.2, 9.3, . . . 9.8, 9.9, 10 mg/kg of body weight. Angiotensin II receptor 1 (AT-1) antagonist, preferably telmisartan may be administered once twice or trice a day in a daily dosage as mentioned above.

In cases when angiotensin II receptor 1 (AT-1) antagonist is administered by parenteral route, said angiotensin II receptor 1 (AT-1) antagonist, preferably telmisartan is administered in a dosage of about 0.01 to about 4 mg/kg of body weight. Preferably, said therapeutically effective amount of such angiotensin II receptor 1 (AT-1) antagonist is about 0.05 to about 3 mg/kg of body weight, even more preferably about 0.1 to about 2.5 mg/kg of body weight, even more preferably about 0.15 to about 2.0 mg/kg of body weight, even more preferably about 0.2 to about 1.5 mg/kg of body weight, most preferred about 0.25 to about 1.25 mg/kg of body weight. Thus, said therapeutically effective amount of such angiotensin II receptor 1 (AT-1) antagonist is for example 0.01, 0.02, 0.03, . . . 0.08, 0.09, 0.1, etc.; 0.11, 0.12, 0.13, . . . 0.18, 0.19, 0.2, etc.; 0.21, 0.22, 0.23, . . . 0.28, 0.29, 0.3 etc. . . . ; 0.81, 0.82, 0.83, . . . 0.88, 0.89, 0.9 etc.; 0.91, 0.92, 0.93, . . . 0.98, 0.99, 1.0 etc.; 1.01, 1.02, 1.03, . . . 1.08, 1.09, 1.1 etc.; . . . 1.1, 1.2, 1.3, . . . 1.8, 1.9, 2.0 etc.; 2.1, 2.2, 2.3, . . . 2.8, 2.9, 3.0 etc.; 3.1, 3.2, 3.3, . . . 3.8, 3.9, 4 mg/kg of body weight. Angiotensin II receptor 1 (AT-1) antagonist, preferably telmisartan may be administered once twice or trice a day in a daily dosage as mentioned above.

In cases when angiotensin II receptor 1 (AT-1) antagonist, preferably telmisartan is administered by oral, rectal, nasal or inhalative route a dosage of about 0.03 to about 10 mg/kg of body weight is preferred. Preferably, said therapeutically effective amount of such angiotensin II receptor 1 (AT-1) antagonist is about 0.10 to about 8 mg/kg of body weight, even more preferably about 0.20 to about 7.5 mg/kg of body weight, even more preferably about 0.25 to about 7.0 mg/kg of body weight, even more preferably about 0.25 to about 6.0 mg/kg of body weight, most preferred about 0.25 to about 5 mg/kg of body weight. Thus, said therapeutically effective amount of such angiotensin II receptor 1 (AT-1) antagonist is for example 0.03, 0.04, 0.05, . . . 0.08, 0.09, 0.1, etc.; 0.11, 0.12, 0.13, . . . 0.18, 0.19, 0.2, etc.; 0.21, 0.22, 0.23, . . . 0.28, 0.29, 0.3 etc. . . . ; 0.81, 0.82, 0.83, . . . 0.88, 0.89, 0.9 etc.; 0.91, 0.92, 0.93, . . . 0.98, 0.99, 1.0 etc.; 1.01, 1.02, 1.03, . . . 1.08, 1.09, 1.1 etc.; . . . 1.1, 1.2, 1.3, . . . 1.8, 1.9, 2.0 etc.; 2.1, 2.2, 2.3, . . . 2.8, 2.9, 3.0 etc.; . . . ; 8.1, 8.2, 8.3, . . . 8.8, 8.9, 9.0 etc.; 9.1, 9.2, 9.3, . . . 9.8, 9.9, 10 mg/kg of body weight. Telmisartan may be administered once twice or trice a day in a daily dosage as mentioned above.

According to another aspect of the invention, the present invention relates a method for the prophylaxis or treatment of a systemic disease in cats, preferably of chronic kidney disease, e.g. chronic renal failure, wherein the method comprising administration of a therapeutically effective amount of angiotensin II receptor 1 (AT-1) antagonist (sartan), preferably telmisartan or pharmaceutically acceptable salt thereof, to that cat in need of such a treatment, wherein the therapeutically effective amount of such angiotensin II receptor 1 (AT-1) antagonist is administered in a therapeutically effective amount that result in an cumulative intravenous concentration of at least 0.025 mg/kg of body weight (bw) Preferably, said angiotensin II receptor 1 (AT-1) antagonist (sartan), preferably telmisartan is administered to an cumulative intravenous concentration of at least 0.05 mg/kg of bw, more preferably of 0.1 mg/kg of bw, even more preferably 0.15 mg/kg of bw even more preferably 0.2 mg/kg of bw, even more preferably 0.25 mg/kg of bw, even more preferably 0.40 mg/kg of bw, even more preferably 0.5 mg/kg of bw, even more preferably 0.75 mg/kg of bw, even more preferably 1 mg/kg of bw. Upper limits of cumulative intravenous concentration of about 1 mg/kg of bw are well tolerable, however, cumulative intravenous concentrations of up to 5, 4, 3 and 2 mg/kg of bw are also within the meaning of the present invention as well as any further higher non-toxic cumulative intravenous concentration of said angiotensin II receptor 1 (AT-1) antagonist (sartan). A person skilled in the art, in view of the teaching given herein, is entitled to estimate that upper non-toxic cumulative intravenous concentration by standard techniques.

Optionally, the angiotensin II receptor 1 (AT-1) antagonist (sartan), preferably telmisartan can be administered in combination with other drugs. Such other drugs are, for example Ca-channel blockers (e.g. Amlodipine), beta-blockers (e.g. Atenolol, Carvediol), cardiotonic-Ca-sensitising agents (e.g. Pimobendan, Levosimendan), selective If-current inhibitors (i.e. Cilobradine, Ivabradine), ACE inhibitors (e.g. ramipril, benazepril, enalapril); anti-obesity drugs (such as Amphetamine derivatives, Sibutramine, Orlistat, Rimonabat) and the like. Thus, according to another aspect, the present invention relates to a method for the prophylaxis or treatment of a systemic disease in cats, preferably of chronic kidney disease, e.g. chronic renal failure, wherein the method comprising administration of a therapeutically effective amount of angiotensin II receptor 1 (AT-1) antagonist (sartan), preferably telmisartan or pharmaceutically acceptable salt thereof, together with another active substance, to that cat in need of such a treatment, wherein said further active substance is a Ca-channel blocker (e.g. Amlodipine), beta-blocker (e.g. Atenolol, Carvediol), cardiotonic-Ca-sensitising agent (e.g. Pimobendan, Levosimendan), selective If-current inhibitor (i.e. Cilobradine, Ivabradine), ACE inhibitor (e.g. ramipril, benazepril, enalapril); an anti-obesity drug (such as Amphetamine derivatives, Sibutramine, Orlistat, Rimonabat) and the like.

Telmisartan and the other active compounds can be orally administered in a wide variety of different dosage forms, i.e., they may be formulated with various pharmaceutically acceptable inert carriers in the form of tablets, capsules, lozenges, troches, hard candies, powders, sprays, aqueous suspensions, elixirs, syrups, and the like. Such carriers include solid diluents or fillers, sterile aqueous media and various non-toxic organic solvents. Moreover, such oral pharmaceutical formulations can be suitably sweetened and/or flavored by means of various agents of the type commonly employed for such purposes. In general, the compounds of this invention are present in such oral dosage forms at concentration levels ranging from about 0.5% to about 90% by weight of the total composition, in amounts which are sufficient to provide the desired unit dosages. Other suitable dosage forms for the compounds of this invention include controlled release formulations and devices well known to those who practice in the art.

For purposes of oral administration, tablets containing various excipients such as sodium citrate, calcium carbonate and calcium phosphate may be employed along with various disintegrants such as starch and preferably potato or tapioca starch, alginic acid and certain complex silicate, together with binding agents such as polyvinylpyrrolidone, sucrose, gelatin and acacia. Additionally, lubricating agents such as magnesium stearate, sodium lauryl sulfate and talc or compositions of a similar type may also be employed as fillers in soft and hard-filled gelatin capsules; included lactose or milk sugar as well as high molecular weight polyethylene glycols. When aqueous suspensions and/or elixirs are desired for oral administration, the essential active ingredient therein may be combined with various sweetening or flavoring agents, coloring matter or dyes and, if so desired, emulsifying agents and/or water, ethanol, propylene glycol, glycerin and various like combinations thereof.

For purposes of parenteral administration, solutions of the compounds in sesame or peanut oil or in aqueous propylene glycol may be employed, as well as sterile aqueous solutions of the corresponding pharmaceutically acceptable salts. Such aqueous solutions should be suitably buffered if necessary, and the liquid diluent rendered isotonic with sufficient saline or glucose. These particular aqueous solutions are especially suitable for intravenous, intramuscular and subcutaneous injection purposes. In this connection, the sterile aqueous media employed are readily obtained by standard techniques well known to those skilled in the art. For instance, distilled water is ordinarily used as the liquid diluent and the final preparation is passed through a suitable bacterial filter such as a sintered glass filter or a diatomaceous earth or unglazed porcelain filter. Preferred filters of this type include the Berkefeld, the Chamberland and the Asbestos Disk-Metal Seitz filter, wherein the fluid is sucked into a sterile container with the aid of a suction pump. The necessary steps should be taken throughout the preparation of these inject-able solutions to insure that the final products are obtained in a sterile condition.

For purposes of transdermal administration, the dosage form of the particular compound or compounds may include, by way of example, solutions, lotions, ointments, creams, gels, suppositories, rate-limiting sustained release formulations and devices therefore. Such dosage forms comprise the particular compound or compounds and may include ethanol, water, penetration enhancer and inert carriers such as gel-producing materials, mineral oil, emulsifying agents, benzyl alcohol and the like.

These preformulated combinations of active substances are generally incorporated with one or more formulation adjuvants such as mannitol, sorbitol, xylitol, saccharose, calcium carbonate, calcium phosphate, lactose, croscarmellose sodium salt (cellulose carboxymethylether sodium salt, cross-linked), crospovidone, sodium starch glycolate, hydroxypropylcellulose (low-substituted), maize starch, polyvinylpyrrolidone, copolymers of vinylpyrrolidone with other vinyl derivatives (copovidone), hydroxypropylcellulose, hydroxypropylmethylcellulose, microcrystalline cellulose or starch, magnesium stearate, sodium stearylfumarate, talc, hydroxypropylmethylcellulose, carboxymethylcellulose, cellulose acetate phthalate, polyvinyl acetate, water, water/ethanol, water/glycerol, water/sorbitol, water/polyethyleneglycol, propyleneglycol, cetylstearyl alcohol, carboxymethylcellulose or fatty substances such as hard fat or suitable mixtures thereof, into conventional galenic preparations such as plain or coated tablets, capsules, powders, suspensions or suppositories.

Tablets may be obtained for example by mixing the active substance or substances with one or more excipients and subsequently compressing them. The tablets may also consist of several layers. Examples of excipients are:
  inert diluents such as mannitol, sorbitol, xylitol, saccharose, calcium carbonate, calcium phosphate and lactose;
  disintegrants such as croscarmellose sodium salt (cellulose carboxymethylether sodium salt, cross-linked), crospovidone, sodium starch glycolate, hydroxypropylcellulose (low-substituted) and maize starch;
  binders such as polyvinylpyrrolidone, copolymers of vinylpyrrolidone with other vinyl derivatives (copovidone), hydroxypropylcellulose, hydroxypropylmethylcellulose, microcrystalline cellulose or starch;
  lubricants such as magnesium stearate, sodium stearyl fumarate and talc;
  agents for achieving delayed release such as hydroxypropylmethylcellulose, carboxymethylcellulose, cellulose acetate phthalate and polyvinyl acetate; and
  pharmaceutically permitted colourings such as coloured iron oxides.

Furthermore, if telmisartan is used in combination with another drug used for the prophylaxis or treatment of a systemic disease, preferably of chronic kidney disease, e.g. chronic renal failure in cats, the pharmaceutical composition according to the invention may be a kit of parts which comprises:
  a first containment containing a pharmaceutical composition comprising a therapeutically effective amount of telmisartan or a physiologically acceptable salt thereof and one or more pharmaceutically acceptable diluents and/or carriers; and a second containment containing another drug used for the prophylaxis or treatment of a systemic disease, preferably chronic renal failure, or a physiologically acceptable salt thereof and one or more pharmaceutically acceptable diluents and/or carriers.

A preferred kit of parts comprises one or more Ca-channel blockers (e.g. Amlodipine), beta-blockers (e.g. Atenolol, Carvediol), cardiotonic-Ca-sensitising agents (e.g. Pimobendan, Levosimendan), selective If-current inhibitors (i.e. Cilobradine, Ivabradine), ACE inhibitors (e.g. ramipril, benazepril, enalapril); anti-obesity drugs (such as Amphetamine derivatives, Sibutramine, Orlistat, Rimonabat) and the like, in the second containment.

According to a further aspect, the present invention also relates to the use of an angiotensin II receptor 1 (AT-1) antagonist (sartan), preferably of telmisartan for the manufacture of a pharmaceutical composition comprising a therapeutically effective amount of said angiotensin II receptor 1 (AT-1) antagonist for the treatment of a systemic disease in cats.

Preferably the systemic disease is selected from the group of cardiovascular diseases, such as dilated cardiomyopathy (DCM), mitral valve insufficiency (MI), hypertrophic cardiomyopathy (HCM) and other acquired or hereditary heart diseases, systemic hypertension, for example hypertension associated with renal diseases, chronic kidney disease and other vascular diseases, metabolic disorders like diabetes mellitus. As mentioned above, chronic kidney disease, preferably chronic renal failure is most preferred.

Preferred sartans are those mentioned in an exemplarily manner supra. Most preferred is the use of telmisartan or any pharmaceutically acceptable salt thereof, such as Micardis®. The preferred doses which can be used according to the invention are those mentioned supra. Preferred administration routes are orally, bucally, parenterally, nasally, rectally or topically, whereas the oral administration being most preferred. Parenteral administration may include subcutaneous, intravenous, intramuscular and intrasternal injections and infusion techniques.

EXAMPLES

The following examples serve to further illustrate the present invention; but the same should not be construed as a limitation of the scope of the invention disclosed herein.

Example 1

The aim of this exploratory study was to investigate the pharmacokinetic behaviour in plasma and the absolute bioavailability of telmisartan in male and female cats following a single oral or intravenous administration.

Four clinically healthy male and female domestic short hair cats (HsdCpb: CADS) with a body weight range of 2.6-4.2 kg were used in this study. The animals were randomly allocated to 2 groups, 2 animals per group. The study was designed as a 2×2 cross-over trial (i.e. two periods, days 1 and 15) in which the test article telmisartan was given by single oral or intravenous administration at a dose of 1 mg/kg body weight.

Blood samples were drawn at 0 h (i.e. prior to treatment), 5 (after i. v. injection only), 15, 30 and 60 min as well as 2, 4, 8, 24, 72 and 96 h after each treatment. Clinical observations were also conducted at these time points. Plasma samples were sent to the analytical laboratory and analysed there using a validated method. The plasma levels measured in each animal were subjected to various pharmacokinetic calculations.

The results of this study may be summarised as follows:

No specific clinical signs were noted during the entire course of the study.

Pharmacokinetic analyses for telmisartan revealed the following results:

| | | Route of Administration | |
|---|---|---|---|
| Parameter | | oral | i.v. |
| t max [hour] | mean | 0.438 | — |
| C max [ng/ml] | mean | 138.10 | — |
| AUC 0 → ∞ [ng · h/ml] | mean | 150.426 | 384.751 |
| AUC 0→ ∞ [ng · h/ml] | mean | 138.598 | 375.945 |
| t ½ [hour] | mean | 2.169 | 2.252 |
| Cl/f or Cl [ml/min · kg] | mean | 171.588 | 45.535 |
| V/f or V [l/kg] | mean | 20.453 | 8.856 |
| MRT [hour] | mean | 1.969 | 0.789 |

The points estimate for the absolute bioavailability were 0.316 for AUC 0→t and 0.336 for AUC 0→∞ with respective 95% confidence intervals of 0.086-1.165 and 0.0.90-1.245. Individual data showed that the bioavailability was clearly lower in animal no. 101 (i.e. 0.116 for AUC 0→∞) in comparison with the other animals (i.e. 0.387-0.582).

The test article telmisartan was well tolerated after a single oral or intravenous administration to cats at a dose of 1 mg/kg body weight.

Mean plasma concentrations increased until 15-30 min after oral administration of telmisartan and declined rapidly afterwards. No quantifiable plasma concentrations could be found at 24 h after both routes, orally and intravenously.

The absolute bioavailability after oral administration was found to be 33%.

Example 2

The aim of this study was to investigate the effects of an escalating intravenous dose of telmisartan on the blood pressure response of anaesthetised cats after administration of angiotensin II. The originally intended endpoint of the study was to find a dose of telmisartan which inhibits ≥90% of the angiotensin blood pressure response.

Four clinically healthy adult male and female domestic short hair cats (HsdCpb: CADS) with a body weight range of 2.5-3.5 kg were used in this study. The animals were anaesthetised with sodium pentobarbital and anaesthesia was sustained by continuous infusion of diluted anaesthetic. A catheter was inserted into a carotid artery and connected to a pressure transducer for registration of the arterial pressure. Another catheter was placed into the femoral vein for administration of angiotensin II (A2) or the test article telmisartan. The systolic and diastolic blood pressure [mmHg] in the carotid artery were recorded and analysed at discrete intervals as described below.

At first, the diastolic blood pressure was registered 6 times every 5 minutes. The mean of these 6 measurements were set as the baseline blood pressure. Then two bolus injections of A2 were administered at a dose of 0.1 μg/kg in an interval of 10 min. The maximum increase in diastolic blood pressure obtained from the second A2-bolus relative to the baseline blood pressure was taken as the control angiotensin II-blood pressure response (i.e. reference value).

Five minutes after the reference value was obtained, the first injection of telmisartan was administered. Thirty minutes later the diastolic blood pressure was recorded, immediately followed by bolus injection of A2 at a dose of 0.1 μg/kg and the maximum increase in diastolic blood pressure was obtained. This procedure was to be repeated accordingly until the intended endpoint of the experiment (i.e. an A2-pressure response ≤10% of the control A2-pressure response corresponding to ≥90% inhibition) was reached. During the course of the experiment it had been shown that the dose of telmisartan had to be increased at single time points in order to increase the effect. In addition, the endpoint of a 90% inhibition could not be reached in 3 of 4 animals even after several consecutive steps as described above so that the experiment was terminated in these individual animals before. At the end of the experiment, the anaesthetised animals were euthanized with an overdose of sodium pentobarbital.

The results of this study may be summarised as follows (see FIG. 1):

The mean baseline diastolic blood pressure of the individual animals ranged from 82-99 mmHg and the control angiotensin II-blood pressure response was between 34 and 63 mmHg.

After treatment with telmisartan, the response pattern was similar in 3 animals (i.e. animal nos. 102, 151, 152). In these animals the maximal inhibition of the blood pressure increase relative to the control angiotensin II-blood pressure response was roughly 80-95% in contrast to 50% inhibition in animal no. 101.

However, the final cumulative dose of the test article was only 0.1 mg/kg in this animal whereas this dose ranged between 0.34 and 0.4 mg/kg in the other animals.

In animal no. 101 the maximum effect of 50% inhibition was reached at a cumulative dose of 0.05 mg/kg. In animal nos. 102 and 152 a 73% inhibition was already reached after the $1^{st}$ dose of 0.04 and 0.02 mg/kg, respectively. In animal no. 151 the same inhibition of 73% was reached at a cumulative dose of 0.04 mg/kg. In all 4 animals, further escalation of the dose did not produce markedly higher effects which were appropriately related to the increase of the dose.

In conclusion, escalating intravenous doses of the test article telmisartan led to an inhibition of the diastolic blood pressure increase in anaesthetised cats after administration of angiotensin II.

An inhibition of 73% was found at the cumulative dose of 0.04 mg/kg telmisartan in 3 of 4 animals. In one animal, a maximum inhibition of 50% was observed at a cumulative dose of 0.05 mg/kg. In all 4 animals, further dose escalations did not produce an appropriate dose response relationship.

Example 3

The aim of this blinded controlled, randomised exploratory study was to investigate the safety of telmisartan in male and female cats after repeated oral administration over four weeks.

Twelve clinically healthy approximately 1 year old male and female, domestic short hair cats (HsdCpb: CADS) with a body weight range of 2.5-5.1 kg were used in this study. The animals were allocated to 3 groups, 4 animals per group. All animals were treated with the test article telmisartan or control article (i.e. placebo) once daily on days 0 to 27. The test/control article was administered orally at three different does levels of 0.0 (placebo; group I), 1 (group II) and 3 (group III) mg telmisartan/kg body weight. The bottles with the test/control article looked identical with the exception of the animal no. in order to achieve blinding.

Blood samples for hematology and clinical chemistry were collected from the animals on days—1 (i.e. prior to the first treatment) and again on days 3, 7, 14, 28. Body weights were measured weekly and electrocardiography recording were made on days—1, 14, 21 and 28. A detailed physical examination including determination of rectal temperature and respiratory rate was carried out on days—1, 7, 14, 22 and 28. Systolic blood pressure (once daily) and heart rate (twice daily) were determined five days per week beginning prior to treatment until necropsy. The palatability of the administered article was assessed at various time points throughout treatment using a scoring system. On day 28 of the study, all animals were subjected to necropsy and stomach and kidneys were examined histopathologically. Relevant parameters were analysed using appropriate statistical procedures.

The results of this study can be summarised as follows:

No clinical findings clearly attributable to the treatment with the test article were observed during the entire study period.

Although no significant differences were found the results of the assessment of the palatability might indicate a slightly impaired palatability of the test article formulation. However, the palatability was predominantly good or acceptable in the animals of both treated groups II and III.

Physical and ECG examinations did not reveal treatment-related findings at all time points of investigation.

No significant differences were found in the body weights, rectal temperature, respiratory and heart rates during the course of the study.

The systolic blood pressure was significantly lower in the treated groups II and III compared to the control group I on single occasions after initiation of treatment. In addition, differences of borderline significance were found including the time before treatment. Changes from baseline did not reveal significant differences between treated groups and controls. However, the course of the mean values over time might suggest a tendency of a slight reduction of the systolic blood pressure in groups II and III compared to group I from day 20 onwards.

No treatment-related differences were found between treated groups and the concurrent controls in the haematological and clinical chemistry parameters including the differential leukocyte count on each day of examination during the study. Urinalysis did also not provide evidence of a treatment effect.

No animal showed any specific finding during necropsy.

Histopathology revealed a few findings in stomach and kidneys but there were no histopathological findings considered to be associated with the treatment.

Due to the exploratory nature of this study the number of animals per treatment group was rather low. Taking this fact into consideration the results of the present study may permit the following conclusions:

A slightly impaired palatability of the test article formulation containing telmisartan might be identified.

The course of the mean values over time might suggest a tendency of a slight reduction of the systolic blood pressure in the animals treated with telmisartan towards the end of the study period.

The test article telmisartan was well tolerated after repeated oral administration over 4 weeks to cats at doses of 1 and 3 mg/kg body weight.

What is claimed:

1. A method for the treatment of chronic kidney disease and/or hypertension in a cat in need thereof, the method comprising daily administration of a therapeutically effective amount of an angiotensin II receptor 1 (AT-1) antagonist (sartan) or a pharmaceutically acceptable salt thereof to the cat, wherein the sartan is selected from the group consisting of candesartan, eprosartan, irbesartan, losartan, tasosartan, telmisartan, and valsartan, and the therapeutically effective amount of the sartan is from about 0.75 to about 5.0 mg/kg of body weight.

2. The method of claim 1, wherein the systemic disease is chronic kidney disease.

3. The method of claim 2, wherein the sartan is selected from the group consisting of irbesartan, losartan, and telmisartan.

4. The method of claim 1, wherein the systemic disease is hypertension.

5. The method of claim 1, wherein the sartan is telmisartan.

6. The method of claim 1, wherein the method further comprises administration of at least one other drug to the cat in need of such a treatment.

7. The method of claim 6, wherein the other drug is selected from the group consisting of Ca-channel blockers, beta-blockers, cardiotonic-Ca-sensitising agents, selective If-current inhibitors, ACE inhibitors, and anti-obesity drugs.

8. The method of claim 1, wherein the daily administration is an oral administration.

9. The method of claim 1, wherein the daily administration is a rectal administration, a nasal administration or an inhalative administration.

10. The method of claim 1, wherein the daily administration of the therapeutically effective amount is provided in a single dose.

11. The method of claim 1, wherein the daily administration of the therapeutically effective amount is provided in a plurality of doses.

12. The method of claim 1, wherein the therapeutically effective amount of the sartan is administered daily for a treatment period of over 4 weeks.

13. The method of claim 1, wherein the therapeutically effective amount of the sartan is administered daily for a treatment period comprising a plurality of days, and the daily dosage amount administered to the cat is varied over the treatment period.

14. The method of claim 1, wherein the therapeutically effective amount of the sartan is no greater than 3.0 mg/kg of body weight.

* * * * *